United States Patent
Scott

(10) Patent No.: US 7,457,714 B2
(45) Date of Patent: Nov. 25, 2008

(54) AUTOCALIBRATED MULTIPHASE FLUID CHARACTERIZATION USING EXTREMA OF TIME SERIES

(75) Inventor: Bentley N. Scott, Garland, TX (US)

(73) Assignee: Phase Dynamics, Inc., Richardson, TX (US)

(*) Notice: Subject to any disclaimer, the term of this patent is extended or adjusted under 35 U.S.C. 154(b) by 0 days.

(21) Appl. No.: 11/490,541

(22) Filed: Jul. 20, 2006

(65) Prior Publication Data
US 2007/0038399 A1 Feb. 15, 2007

Related U.S. Application Data

(60) Provisional application No. 60/721,233, filed on Sep. 28, 2005, provisional application No. 60/700,970, filed on Jul. 20, 2005.

(51) Int. Cl.
*G01F 1/00* (2006.01)
*G01F 25/00* (2006.01)

(52) U.S. Cl. .................................................. 702/100
(58) Field of Classification Search .................. 702/100
See application file for complete search history.

(56) References Cited

U.S. PATENT DOCUMENTS

| | | | |
|---|---|---|---|
| 5,259,239 A | 11/1993 | Gaisford | |
| 5,260,667 A | 11/1993 | Garcia-Golding et al. | |
| 5,576,974 A | 11/1996 | Marrelli et al. | |
| 5,654,502 A | 8/1997 | Dutton | |
| 6,234,030 B1 | 5/2001 | Butler | |
| 6,318,156 B1 | 11/2001 | Dutton et al. | |
| 6,327,914 B1 | 12/2001 | Dutton | |
| 2003/0011386 A1* | 1/2003 | Xie et al. ................ 324/694 |

(Continued)

FOREIGN PATENT DOCUMENTS

WO WO 00/77739 A1 12/2000

OTHER PUBLICATIONS

Dutton, Robert E., "Automatic Well Test System and Method of Operating the Same", PCT/US96/20890, Dec. 23, 1996, WO 97/24615, Jul. 10, 1997.

(Continued)

*Primary Examiner*—Michael P. Nghiem
*Assistant Examiner*—Cindy H Khuu
(74) *Attorney, Agent, or Firm*—Groover & Associates

(57) ABSTRACT

Systems and methods for determining the fraction of a first phase of a multiphase fluid flow stream, such as the amount of water in crude petroleum oil flowing from a production well or container. An electrical property, such as permittivity, and a physical property, such as density, are used as the basis of the improved characterization. The method is particularly well-suited to reduce salinity-dependent uncertainties for wells experiencing high water cuts. A time series of measurements is collected, and the extrema of the observed values are used to generate a hindsight auto-calibration and correction to the other values using knowledge of the degree of uncertainty in the measurements caused by variable salinity and variable phase state of the multiphase fluid. The hindsight auto-calibration and corrections thus permit more accurate measurements of the instantaneous and the cumulative amounts of each phase in the multiphase fluid flow stream.

20 Claims, 8 Drawing Sheets

U.S. PATENT DOCUMENTS

2004/0129874 A1* 7/2004 Torgersen et al. ............ 250/255
2005/0081643 A1  4/2005 Mattar et al.
2007/0157708 A1* 7/2007 Scott .......................... 73/61.44
2007/0239402 A1* 10/2007 Scott .......................... 702/189

OTHER PUBLICATIONS

Mohajer, Kim et al, "Device for Determining Compositiion of a Fluid Mixture", PCT/US05/015341, Mar. 5, 2005, WO 2005/109012A1 Nov. 17, 2005.

* cited by examiner

AUTOCALIBRATED MULTIPHASE FLUID CHARACTERIZATION USING EXTREMA OF TIME SERIES

CROSS-REFERENCE TO RELATED APPLICATIONS

This application claims priority from U.S. provisional patent application 60/700,970 filed on Jul. 20, 2005 and 60/721,233 filed on Sep. 28, 2005.

BACKGROUND AND SUMMARY OF THE INVENTION

The present application relates to systems and methods for measuring the amount of one phase in a mixture of phases, and more particularly to measuring the amount of water present in crude petroleum oil.

The following paragraphs contain some discussion, which is illuminated by the innovations disclosed in this application, and any discussion of actual or proposed or possible approaches in these paragraphs does not imply that those approaches are prior art.

Background: Water Cut Analyses in Oil Processing

The chemical and physical characterization of crude, partially refined, and fully refined petroleum products is a common practice in the petroleum industry. Characterizations such as compositional and physical property determinations are used for a variety of purposes. One of their more important uses is when they are done in combination with hydrocarbon well testing to assist in optimizing oil production from a single or series of hydrocarbon wells. Another important use is during the transfer of crude petroleum oil, as occurs during the production, transport, refining, and sale of oil. Specifically, it is well know to a person having ordinary skill in the art of petroleum engineering that crude petroleum oil emerging from production wells can contain large amounts of water, ranging from generally about 1% to as high as about 95% water. This value is known as the water cut ("WC").

Hydrocarbon well optimization methods include adjusting the well operating parameters and employing reservoir stimulation techniques. Decisions in the use of such optimization methods are greatly enhanced if accurate compositional data of the oil is available, both instantaneously and over time. Specifically, in one context of hydrocarbon well production optimization, it is important to be able to determine the amount of water mixed with the crude oil, which is often present as naturally-produced ground water, water from steam injection, and/or well injection water which has become eventually mixed with the oil as a result of a reservoir stimulation process. Once such stimulation process is known as Steam Assisted Gravity Drain stimulation ("SAGD"). Another is the "Huff and Puff" stimulation method where steam is intermittently injected into the reservoir. Different types of stimulation processes can have different phase states upon start-up of the well. Additionally, a result in steam-assist wells is that the salinity of the aqueous phase varies across the steam-assist cycle, usually starting at a low value and climbing throughout the cycle to a high value.

When water is pumped to the surface of the Earth along with the crude oil, producers often attempt to physically separate the water from the oil, because the water can corrode pipes and damage down-stream processing equipment. Further, the water has no value relative to the oil and in-fact can become a disposal or environmental problem wherever it is finally removed. Water-oil "separators" or liquid-liquid decanters are thus often used, before the crude oil is further transported from a well site or tank farm. However, the efficiency of such separators in achieving two pure streams of oil and water is often not 100%, and free water is still frequently entrained in the crude oil as it enters storage, in the range of about 0.10% to about 5%.

Another complicating issue is that gases are almost always present in crude oil as it emerges from the wellhead. This gas is usually natural gas consisting of the lighter hydrocarbon fractions such as methane, ethane, propane, and butane, and can further complicate the chemical and physical assay and characterization of the crude oil stream. Sometimes, carbon dioxide is also present, either naturally-occurring or because it is frequently used in reservoir stimulation. Additionally, gases are often used in varying proportions to lift oil from a well. Gas-liquid separators are often employed to remove the gas fraction and to allow it to be separately measured from the liquid phase. However, again, the efficiency of such separators in achieving two pure streams of liquid and gas is often not 100%, and free gas is sometimes entrained in the crude oil liquid fraction.

The accurate determination of water content and validation of the amount of water in crude oil is particularly important during the taxation of crude oil and the sale of crude oil, where the owner or seller of the oil does not want to pay taxes on water and the customer does not want to pay the price of oil for water. Such determinations and validations can be conducted on-line and off-line during petroleum processing.

The offline method involves physically sampling the stream and analyzing it in a laboratory setting. In the petroleum industry, the sampling is usually done using a composite sampler which automatically opens a sample valve attached to a pipeline at some pre-determined frequency to collect an aggregate sample into a sample container. The objective is to collect a sample which is representative of the entire lot of petroleum under consideration. After collection, the composite sample is usually picked up by a person and taken to a laboratory. The composite sample is then "sampled" to prepare aliquots, or sub-divisions of the composite sample, for each of the various characterizations, or analysis methods, to be used.

Three off-line analytical methods are commonly used for determining the water content of crude oil. These are the centrifuge method, the distillation method, and the titration method. See the American Petroleum Institute ("API") Manual of Petroleum Measurement Standards, Chapter 10. The distillation and titration methods are relatively accurate, but are plagued by long analysis times and not suitable for use in the field or at the point of sale. The centrifuge method is quicker, but almost always under-reports the amount of water present. The American Society for Testing of Materials has reported the standard analytical errors for water content measurements using the three methods. The repeatability errors are 0.11% for the distillation method (see ASTM D4006), 0.15% for the titration method (see ASTM D4377), and 0.28% for the centrifuge method (see ASTM D4007).

Note that composite petroleum samplers and the associated analytical methods have other kinds of problems and disadvantages other than, for example, meeting a desired accuracy for a given determination. For example, results for composite samplers are typically only available at the end of a batch or a test, and there is no recourse if something goes wrong with the sampling system during the sampling process. At the end of the sampling and analysis, only a single number is available to consider. Additionally, the exposure of personnel to hazardous liquids associated with processing the samples is undesirable. Thus, the petroleum industry has continued to seek other methods that provide the required accuracy, speed, and safety.

Accordingly, the use of rapid on-line instruments such as densitometers, capacitance probes, radio frequency probes, and electromagnetic characterization systems (including those which are referred to, for historical reasons, as "microwave analyzers") to measure water content of petroleum products is becoming more common. Besides providing increasingly accurate determinations of water content, real time water content results via on-line methods can provide beneficial operational advantages. Knowledge of when water becomes present in petroleum as it is being produced and the magnitude of the quantity of the water may provide an opportunity to remove the water before it reaches a transport pipeline, storage vessel, or shipping tanker. Additionally, the real time data may show if the water is detected in several short periods of time or if it is present across the entire load of the petroleum. Furthermore, real time analyzers may be used as a comparison to the results provide by composite samplers. Finally, on-line measurements of, for example, physical and electrical properties, via instrumentation reduces the need human involvement in the process of characterizing a multiphase fluid mixture.

Background: On-Line Measurements for Density and Electromagnetic Characterizations On-line densitometers can be used to ascertain the amount of water in petroleum oil. One on-line density method uses a Coriolis meter. This meter can be installed in the pipeline leaving the well or wells on the way to further processing and storage. Coriolis meters measure the density of a fluid or fluid mixture, and its mass flow rate, using the Coriolis effect. Then, calculations can be performed to indirectly determine the water percentage. For example, a Coriolis meter can measure the density of a water-oil mixture, $\rho_{mixture}$, and then perform a simple calculation method to determine the individual fractions or percentages of the water phase and oil phase. By knowing or assuming the density of the dry oil, $\rho_{dry\ oil}$, and the density of the water phase, $\rho_{water\ phase}$, then a water weight percentage, $\psi_{water}$, can be calculated as follows:

$$\psi_{water\ phase} = ((\rho_{mixture} - \rho_{dry\ oil})/(\rho_{water\ phase} - \rho_{dry\ oil})) \times 100$$

This technique, however, is subject to uncertainty in the validity of the measurement of the percentage water in oil. First, due to natural variations of, for example, the hydrocarbon composition of crude oil, the density of the dry oil can vary significantly from the assumed or inputted value required for the simple calculation. Such a value inputted into a densitometer based on a guess or on history of a given hydrocarbon well. Crude petroleum oils can range from about 800 kilograms per cubic meter ($kg/m^3$) to about 960 $kg/m^3$. Further, the water encountered in hydrocarbon well production is most often saline. This salinity is subject to variability, ranging from about 0.1% by weight salt to about 28%. This results in a variation in the density of the water phase from about 1020 $kg/m^3$ to about 1200 $kg/m^3$. Again, this value would be inputted into a densitometer based on a previously-known laboratory number or on the history of a given well.

Note also that an entrained gas phase, as is sometimes present as described previously, can dramatically affect the density of a petroleum stream as measured by a Coriolis meter, unless a precise correction method is applied for the presence of the gas.

Another technique to determine the water-cut is to use an electromagnetic characterization system (e.g. a "microwave analyzer"), instead of a densitometer, to perform the in-line monitoring of the oil and water mixture.

U.S. Pat. No. 4,862,060 to Scott (the '060 patent), entitled Microwave Apparatus for Measuring Fluid Mixtures and which is hereby incorporated by reference, discloses electromagnetic characterization systems and methods which are most suitable for monitoring water percentages when the water is dispersed in a continuous oil phase.

Note that the change in fluid mixture dielectric properties for a water and oil mixture can be affected by a number of parameters, including not only the percentage of water in oil, but also the individual dielectric constants of the oil phase and the water phase. For example, the dielectric constant of the dry crude oil itself can vary depending on its density and chemical composition. Note that temperature can affect the density of the oil and the water and thus the dielectric properties of each component and the mixture. However, temperature variations can easily be compensated for by using a temperature probe in-contact with the multiphase fluid being characterized to allow referencing to data sets or curves fit to the data sets for different temperatures.

Thus, both the densitometer method ("water-cut by density") and the electromagnetic characterization method ("water-cut by electromagnetic characterization") are subject to uncertainties. One approach to dealing with the uncertainty is to simultaneously use both methods to characterize a crude petroleum oil stream for water content. This joint use is practiced commercially. An example is the Compact Cyclone Multiphase Meter ("CCM") manufactured by Phase Dynamics, Inc. of Richardson, Tex.

When conducting joint densitometry and electromagnetic characterizations of a flow stream of mixtures of water and crude or partially refined petroleum oils, exact values of the electrical and physical properties of the pure water and oil phases are not always known. However, each method can supply estimates of the required values to assist each other in determining water content in petroleum products.

An example of a such a supply of a physical property estimate is disclosed in U.S. patent application Ser. No. 11/273,613, now U.S. Pat. No. 7,334,450, to Bentley N. Scott entitled Methods for Correcting On-Line Analyzer Measurements of Water Content in Petroleum, and is hereby incorporated by reference, and hereinafter referred to as Scott '613. Scott '613 discloses that because a conventional electromagnetic characterization analyzer is usually shop-calibrated across a range of water contents using a dry oil of a known density, the analyzer will report an erroneous water percentage if the dry oil being measured in the field shifts to a different density than that of the original dry calibration oil. The auto-correction method disclosed in Scott '613 ameliorates this problem. Scott '613 teaches that there is 0.03% water-cut by permittivity error introduced for every 1 $kg/m^3$ shift in actual dry oil density from the dry oil calibration density. It discloses that for water-cuts less than about 5%, the density of the actual dry oil can be adequately estimated for use in calculations by the microwave analyzer by assuming the actual dry oil density is equal to the density of the mixture as measured by the densitometer. This assumption results in a maximum error rate of about 0.23% at about 5% water-cut. This error rate compares favorably to the off-line analytical method error rates previously detailed. For well testing the error is more difficult to define and must be done by statistical methods of pulling a population of samples large enough to find a statistical mean and standard deviation. This method is not well defined and the true error is not known since each sample is an independent one and is subject to many errors with equipment and personnel. Since the lab method does not have a known standard error the resulting data is a measure of the reproducibility of the on line analytical equipment and the laboratory methods and handling of the samples.

Background: Crude Oil Phase Behavior and Electromagnetic Characterizations

Still further uncertainty in conducting on-line characterizations of multiphase fluids such as crude oil can be caused by both the physical chemistry of each of the fluids and the multiphase fluid mixture itself. In the case of liquid-liquid mixtures undergoing mechanical energy input, the mixture usually contains a dispersed phase and a continuous phase. So, in the example of water and oil, the mixture exists as either water-in-oil or an oil-in-water dispersion. When such dispersion changes from aqueous phase continuous to non-aqueous phase continuous, or vice-versa, it is said to "invert the emulsion phase".

Dispersion of one phase into another becomes more stable under mechanical energy input such as agitation, shaking, shearing, or mixing. These resulting physical properties are known as the rheologic properties of the fluids. When the mechanical energy input is reduced or eliminated, coalescing of the dispersed phase can occur, where droplets aggregate into larger and larger volumes. However, these can also be very stable with time depending upon the natural surfactants, densities, temperatures, and salinity of the water. Further, in a substantially static situation (e.g. reduced energy input), heavy phase "settling-out" or stratification can occur under the force of gravity.

Complicated water-oil mixture separation phenomena can sometimes occur as crude oil is pumped from the ground (or from the subsea floor). Because hydrocarbon wells can range in depths to well over 10,000 feet, the oil and any water phase travel in the pipeline for a relatively long period of time before it reaches the wellhead. As the oil and water phases travel to the wellhead, coalescing of each phase can occur, resulting in "slugs" of oil and water emerging from the well rather than a dispersion of, say, small droplets of water in a continuous oil phase. Thus, a well that produces a high level of water can cycle between a span of primarily free water and a span of primarily dry oil. In essence, the vertical column of oil and water in the long well pipe, known as a drill "string", becomes a vertical oil-water separator. As a result, the water builds up in the drill string and is then pushed through as a water "slug" to the wellhead. This kind of well, due to its behavior, is termed a "slugging" oil well.

A further complicating phase-state phenomena of liquid-liquid mixtures is that stable or semi-stable suspensions of dispersed-phase droplets can sometimes occur. This is usually referred to as an emulsion, which can be either stable or semi-stable. Certain substances are known as emulsifiers and can increase the stability of an emulsion, meaning that it takes a longer time for the emulsion to separate into two phases under the force of gravity or using other means. In the case of petroleum oils, emulsifiers are naturally present in the crude oil. For example, very stable emulsions can occur during petroleum processing, as either mixtures of water-in-oil or oil-in-water as a stable emulsion possible even up to 90% water.

Another complicating phenomenon is that the formation of dispersions and emulsions are sometimes "path-dependent." Generally, path-dependence exists when the result of a process depends on its past history, i.e. on the entire sequence of operations that preceded a particular point in time, and not just on the current instantaneous conditions. In the case of emulsions, the process of forming the emulsion can be path dependent because the sequence of phase addition, mixing, and energy inputs can affect which phase becomes the dispersed phase and how stable the resulting emulsion is. Thus, if one does not know the history of the multiphase fluid undergoing dispersion or emulsification, one will not always be able to predict the "state" of the dispersion or emulsion, i.e. which phase is continuous and which is dispersed, even if the proportions of the phases are accurately known at a particular point in time.

In electromagnetically-coupled analyzers, whether a dispersion or emulsion is aqueous-continuous or non-aqueous-continuous has a significant effect on the analyzer's measurements. In the case of aqueous-continuous dispersions or emulsions, the conductivity path established by the aqueous-continuous phase causes a significant change in the measured electromagnetic characterizations relative to the same proportion of phases existing as a non-aqueous-continuous dispersion or emulsion. Additionally, further variations in the conductivity of the aqueous-continuous phase caused, for example, by even relatively small changes in salinity, can significantly affect the measured electromagnetic characterization results. Note that when the non-aqueous or oil phase is continuous, no conductivity path is established (because the droplets are not "connected" to form a continuous conducting circuit), Hence (at low RF frequencies) there is no significant effect on the measurements of an electromagnetic characterization analyzer due to aqueous conductivity. Note also that this is only true when the wavelength of the electromagnetic energy is large compared to the emulsion size. When the emulsion size is larger than one eighth of a wavelength the voltage difference across the emulsion can be significant and therefore a correction must be made with respect to the salinity (conductivity at the frequency of measurement) of the water.

As a particular example of the complex behavior of liquid-liquid mixtures and the impact of that behavior on electrical characterizations such as permittivity analyses, consider FIG. 1B. It is a generalized phase diagram 100 of particular crude petroleum oil and a range of aqueous solutions of varying salinity where the fraction of the water phase, $X_W$, is plotted against the frequency, $f$, as instantaneously read by an electromagnetic characterization microwave analyzer. Note that although the lines are shown as straight lines the relationship between $X_W$ and $f$ may not be strictly linear. To illustrate aspects of the complex behavior of liquid-liquid mixtures, consider starting with a pure oil phase that is under-going a given amount of mechanical energy input, as is encountered when such a fluid is pumped through a restricting valve and is experiencing a pressure drop. This starting composition, on the path independent, oil-continuous line 101, is represented by point 102. Then, an aqueous saline solution could be added to the oil phase to form a mixture of water-in-oil, represented by points on line 101. The relationship between the permittivity frequency and the aqueous phase fraction is determined by the line 101. On this line, the multiphase fluid exists as an oil continuous phase with drops of dispersed aqueous phase. Then, increasing amounts of saline solution can continue to be added, up along line 101 to point 104. At point 104, the dispersion progresses along path dependent line 105 to point 106. At point 106, the dispersion inverts to an aqueous phase continuous dispersion, with an accompanying discontinuity in measured permittivity, jumping to a particular permittivity curve depending to a large extent on the salinity of the aqueous phase. Aqueous phase can continue to be added along salinity iso-lines in zone 107 to path-independency transition level 108. At path-independency transition level 108, path dependency is no longer present as the dispersion moves into zone 109. The fraction of aqueous phase can be increased to 1.00, with the permittivity being dependent on both the salinity and the fraction of the aqueous phase.

It should be noted that in certain emulsions, zone 107 may not exist at all, and line 105 might transition directly to zone 109.

In an another example of possible path dependency, the mixture may begin as a point located some where in a high water cut, path independent, salinity-controlling, aqueous-continuous zone 109. Then, the aqueous fraction could be reduced to path-dependency transition level 110, and further reduced to aqueous fraction 112, along the iso-salinity lines within the high water cut, path dependent, aqueous-continuous zone 111. The iso-salinity lines within zone 111 are shown as dashed lines because they represent salinity levels which may be the same as that in zone 107. Additionally, path-dependency transition level 110 may or may not be equal to path-independency transition level 108.

Next, following the iso-salinity lines through zone 107, the dispersion would invert at aqueous fraction 112, and as aqueous fraction is further reduced, the relationship follows oil-continuous, path-dependent line 113 to point 104.

It should be noted that in certain emulsions or dispersions, zone 111 may not exist at all, and line 113 might transition directly from zone 109.

Thus, for the particular crude oil example above as it is mixed in various proportions with a variable salinity aqueous phase, at least three zones of compositional uncertainty can exist for the permittivity of aqueous-continuous dispersions, of which at least two such zones can be path-dependent. Additionally, at least three discrete curves can further relate the permittivity of oil-continuous mixtures, of which at least two such curves can be path dependent. In addition, the oil continuous region is dependant upon the frequency of operation as to whether salinity has any affect on the relationship with water percentage as described earlier with respect to the wavelength of the electromagnetic energy.

Such complex physical chemistry can lead to numerous uncertainties with regards electromagnetic-characterization-based composition determinations. For example, referring again to FIG. 1B of this application, frequency 114 can in-fact represent two different mixture compositions, 116 and 118, depending on how such compositions were formed, as previously described. Additionally, a particular aqueous fraction 119 can correspond to either an aqueous phase dispersion of varying salinity contents, points 120, each having a corresponding permittivity frequency (not shown) or an oil-continuous phase dispersion of a particular frequency 122.

It has been found that these compositional and permittivity frequency uncertainties can be reduced by using a number of methods, depending somewhat on which zone or curve the mixture state resides in or on. For example, to address the problems of phase inversion uncertainties in aqueous and non-aqueous multiphase mixtures, U.S. Pat. No. 4,996,490 to Scott (the '490 patent), entitled Microwave Apparatus and Method for Measuring Fluid Mixtures and which is hereby incorporated by reference, discloses electromagnetic characterization apparatuses and methods for accommodating phase inversion events. For the example of oil and water mixtures, the '490 patent discloses that whether a particular mixture exists as an oil-in-water or a water-in-oil dispersion can be determined by differences in the reflected microwave power curves in the two different states of the same mixture. Therefore, the '490 patent discloses magnetic characterization apparatuses and methods, including the ability to measure microwave radiation power loss and reflection to detect the state of the dispersion. In further embodiments of that invention, methods are disclosed to compare the measured reflections and losses to reference reflections and losses to determine the state of the mixture as either water-in-oil or oil-in-water, which then allows the proper selection and comparison of reference values relating the measured microwave oscillator frequency to the percentage water. An embodiment of the '490 patent is reproduced from that patent in FIG. 1C.

Thus, referring again to FIG. 1B of this application, for water fraction 119, the apparatus and the method of the '490 patent would be able to identify whether the dispersion is in zone 111 or on line 105. When the composition is on line 105, electromagnetic characterization analyzers using the method of the '490 patent are able to accurately determine the aqueous phase fraction. However, within zone 111, the method of the '490 patent would not be able to accurately distinguish which iso-salinity line the composition correlated to in real time, because alone, the method of the '490 patent has no way of knowing the salinity on a real time basis. Thus, the method of '490 alone would not be able to accurately determine water fraction 118.

One method of correcting for the effects of salinity changes is for an operator to manually measure the salinity of the water phase and input the measurement into the analyzer to allow it to select pre-established offset correction factors, based on the inputted salinity and test-generated calibration curves. FIG. 3 and FIG. 4 show exemplary electromagnetic characterization analyzer offset salinity corrections for a generally low range of salinity, of about 0.1% to 8% salinity, and a high range of salinity, of about 8% to about 28% salinity.

A manual determination of salinity is commonly made using a refractometer to measure the refractive index of the water phase. This index is then correlated to % salinity using a pre-established relationship between % salinity and refractive index. The % salinity is then entered into the analyzer as previously described. The pre-established relationship between % salinity and refractive index can be developed by measuring the refractive index of a series of standardized saline solutions to establish a data reference set and equations can be fitted to the data set.

Sometimes, the refractive index of the aqueous phase cannot be easily determined. For example, the aqueous phase may be so turbid as to prevent an accurate reading from being obtained. Or, in the case of an emulsified system, the refractive index cannot be read unless the system is somehow de-emulsified and allowed to separate into a clear-enough aqueous phase to allow a refractive index to be determined.

Such refractive index measurement techniques or other separate salinity measurement techniques are thus inherently unreliable in systems that are susceptible to emulsification and require additional apparatus, further complicating the total measurement system.

Other laboratory methods will analyze the produced water for ionic content and a "total dissolved solids" and the "equivalent NaCl" contents can be determined. Since different salts i.e. NaCl, KCl, etc. all have different conductivities (and these change with electromagnetic frequency) it is difficult to know what number is appropriate to use. Many times the "total dissolved salts" will be used as equivalent NaCl. These numbers are inexact and will lead to real time errors of measurement. In addition, the samples are always at room temperature and do not reflect the conductivity of the ion at the operating temperature of the production fluids.

Thus, solving the problem of accurately ascertaining and validating the amount of each phase in multiphase mixtures is a long felt requiring a more complete and automated solution. More particularly, there is an increasing need for reduction of uncertainty in the characterization of petroleum as the value of petroleum continues to rise.

The present application discloses systems and methods for determining relative proportions of phases in multiphase fluid flow streams. As live characterization data is collected from a multiphase fluid stream, a time series of measurements results. At least some of the extrema of the time series of data are used to generate a corrective transform or transforms.

In some embodiments (but not necessarily all), the disclosed ideas are used at the wellhead of (or slightly downstream from) a producing hydrocarbon well, to estimate the water-cut in as-produced crude petroleum oil.

In some embodiments (but not necessarily all), the disclosed ideas are used at the wellhead of (or slightly downstream from) a producing hydrocarbon well experiencing high water-cut conditions.

In some embodiments (but not necessarily all), the disclosed ideas are used at the wellhead of (or slightly downstream from) a producing hydrocarbon well to improve the accuracy of the characterization of the hydrocarbon well being tested by recalling previously-made characterizations of the same hydrocarbon well upon re-starting or re-testing of the hydrocarbon well.

In some embodiments (but not necessarily all), the disclosed ideas are used at the wellhead of (or slightly downstream from) a producing hydrocarbon well by first removing essentially all of any gas fraction contained in crude petroleum emerging from the wellhead or from a gas-liquid separator.

In some embodiments (but not necessarily all), the time series of measurements includes joint measurements of an electrical property, such as permittivity, and measurements of a physical property, such as density.

The disclosed innovations, in various embodiments, provide one or more of at least the following advantages:

Some of the disclosed inventions provide auto-calibration or correction methods to reduce the uncertainty caused by variable salinity in an aqueous phase of a multiphase fluid flow stream.

Some of the disclosed inventions provide auto-calibration or correction methods to improve the characterization of a multiphase fluid flow stream using a single characterization apparatus with improved accuracy across the complete range of first phase content.

Some of the disclosed inventions provide more accurate physical or electrical property measurements.

Some of the disclosed inventions provide near-real-time reduction of errors and supply more accurate results to aid in near-real-time decision-making, without requiring multiphase fluid flow stream sampling or off-line labwork conducted on such samples and thus eliminating the cost, lost opportunities, and hazards associated with such sampling.

BRIEF DESCRIPTION OF THE DRAWINGS

The disclosed inventions will be described with reference to the accompanying drawings, which show illustrative, non-limiting embodiments of the invention and which are incorporated in the specification hereof by reference, wherein.

DETAILED DESCRIPTION OF THE PREFERRED EMBODIMENTS

The disclosed innovations of the present application will be described with particular reference to presently preferred embodiments (by way of example, and not of limitation).

Figure 5:
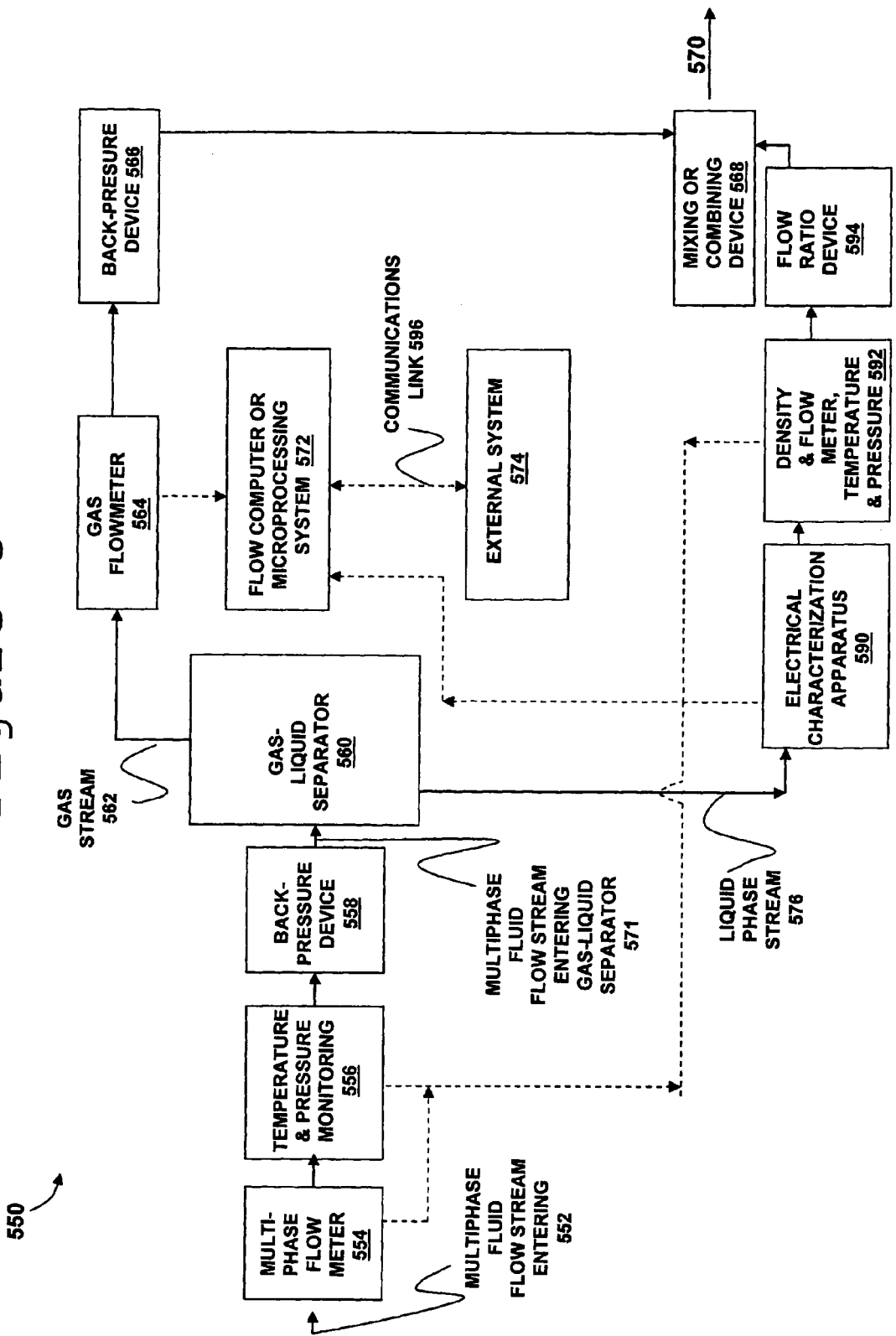
FIG. 5 shows an exemplary multiphase fluid characterization apparatus comprising a liquid-gas separator, an on-line electric property analyzer, a densitometer in the liquid stream, flow meters in both the gas and liquid streams, and a computer or microprocessor system incorporating the method of FIG. 1A and/or the method of FIG. 6, consistent with a preferred embodiment or embodiments.

FIG. 5 shows a characterization system 550 according to an illustrative, non-limiting example of a preferred embodiment consistent with the present application, for characterizing a multiphase fluid, such as the gases and liquid petroleum recovered from a hydrocarbon well or wells. The petroleum may be a liquid stream comprising oil and a water phase, with entrained non-condensed gas. A gas-liquid-liquid multiphase fluid flow stream 552 enters the apparatus. The flow rate of the flow stream can be monitored at 554. Pressure of the flow stream can be monitored at 556. Suitable back pressure, if any, of the flow stream can be maintained by a suitable device at 558. Multiphase flow stream 572 can emerge from the backpressure device of 558 and can enter gas-liquid separator 560 where a condensible and/or non-condensible gas fraction can be separated from the multiphase fluid to a degree consistent with the composition and physical properties of the multiphase fluid and its components, as well as the design and operating parameters of gas-liquid separator 560 as known to a person having ordinary skill in the design and operations of gas-liquid separators. The gas fraction flow stream 562 exits separator 560 and the flow rate, temperature, and pressure can be monitored at 564. Back pressure of flow stream 562, if any, can be maintained by a suitable device at 566.

Gas-liquid production separators are described in Chapter 12 of the third printing of the Petroleum Engineering Handbook, Howard B. Bradley editor-in-chief, Society of Petroleum Engineers, 1992, hereby incorporated by reference. FIGS. 12.23 and 12.25 from the Petroleum Engineering Handbook show schematics of typical production gas-liquid separators as can be used as separator 160.

A liquid-liquid mixture flow stream 576 can be monitored for water-cut at 590 and can be monitored for density, flow rate, temperature, and pressure at 592. The proper representative flow rate ratio of stream 576 to stream 562 can be maintained on stream 576 by a suitable device at 594.

Stream 576 and 562 can be combined in mixing or combining device 568 and then exit system 550 as stream 570.

Figure 1A:
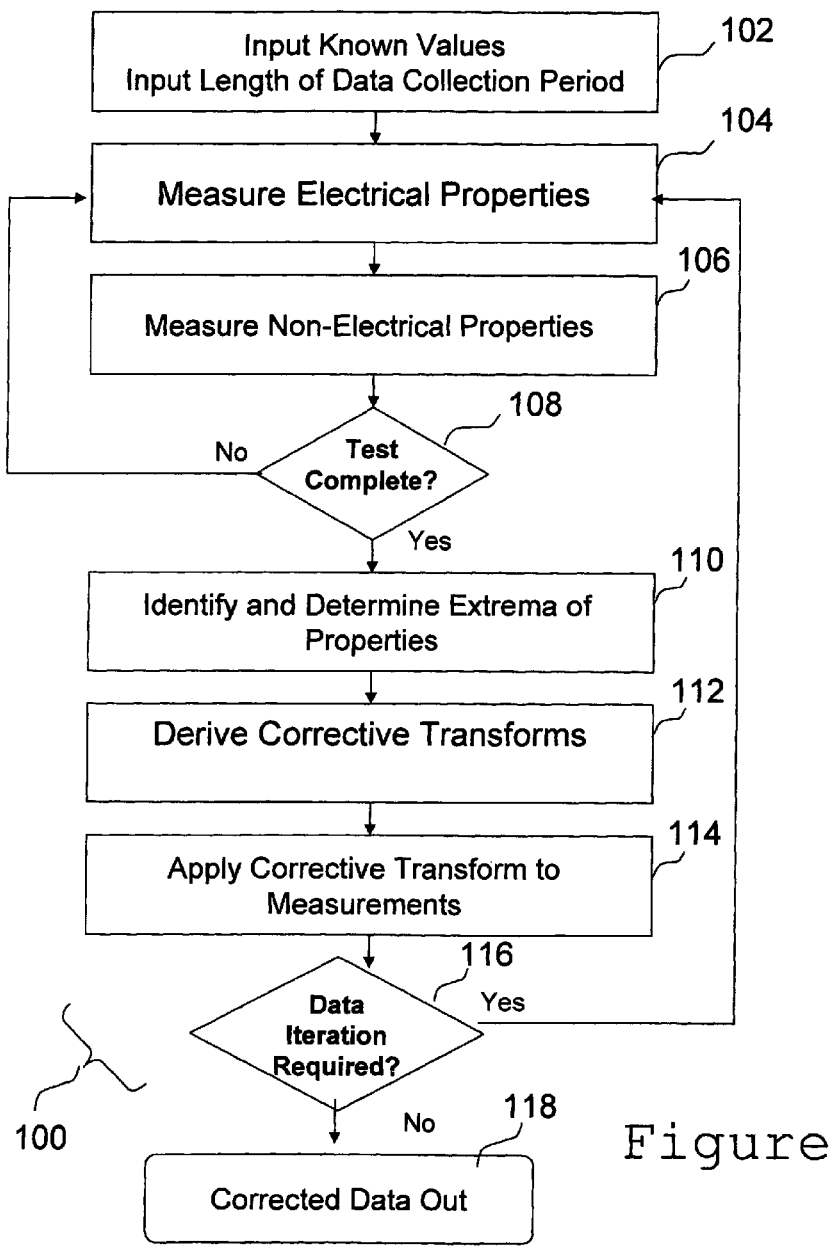
FIG. 1A shows a method for characterizing multiphase fluids which measures and uses extrema of properties to derive a corrective transform or transforms which are then applied to measurements, resulting in the output of corrected data and multiphase fluid characterizations.
Figure 1B:
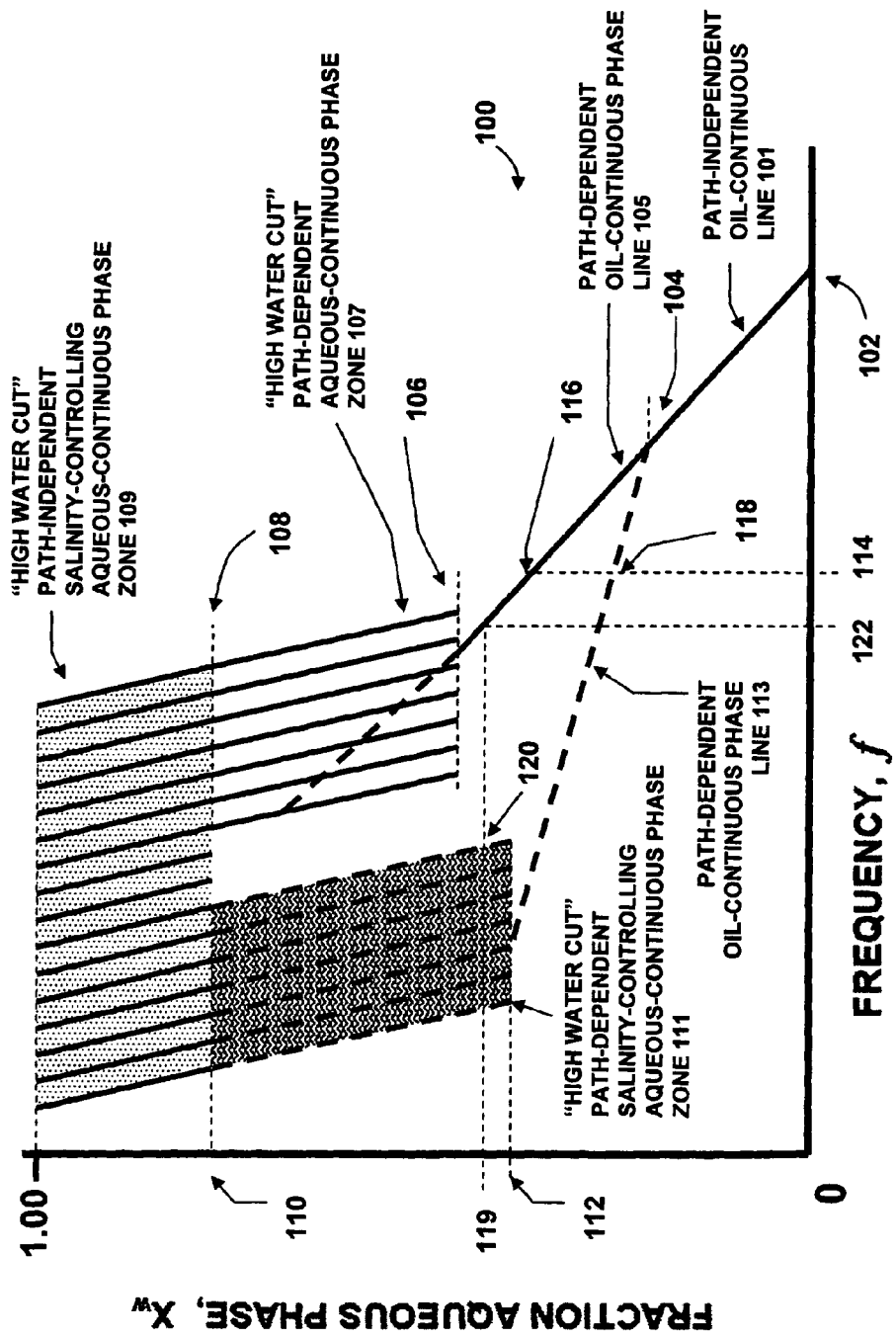
FIG. 1B shows an exemplary generalized phase versus frequency diagram 100 of particular crude petroleum oil and a range of aqueous solutions of varying salinity as previously described.

Measuring components 554, 556, 590, 592, and 564 can all or selectively be electrically coupled to flow computer or microprocessor system 572 which in one embodiment of the present innovations, performs and outputs the calculations of, for example, the method of FIG. 1A. In another embodiment, flow computer or microprocessor system 572 can transmit or output collected measurements to external system 574 where the measurements can be stored or other calculations can be performed, including, for example, the method of FIG. 1A.

Figure 1C:
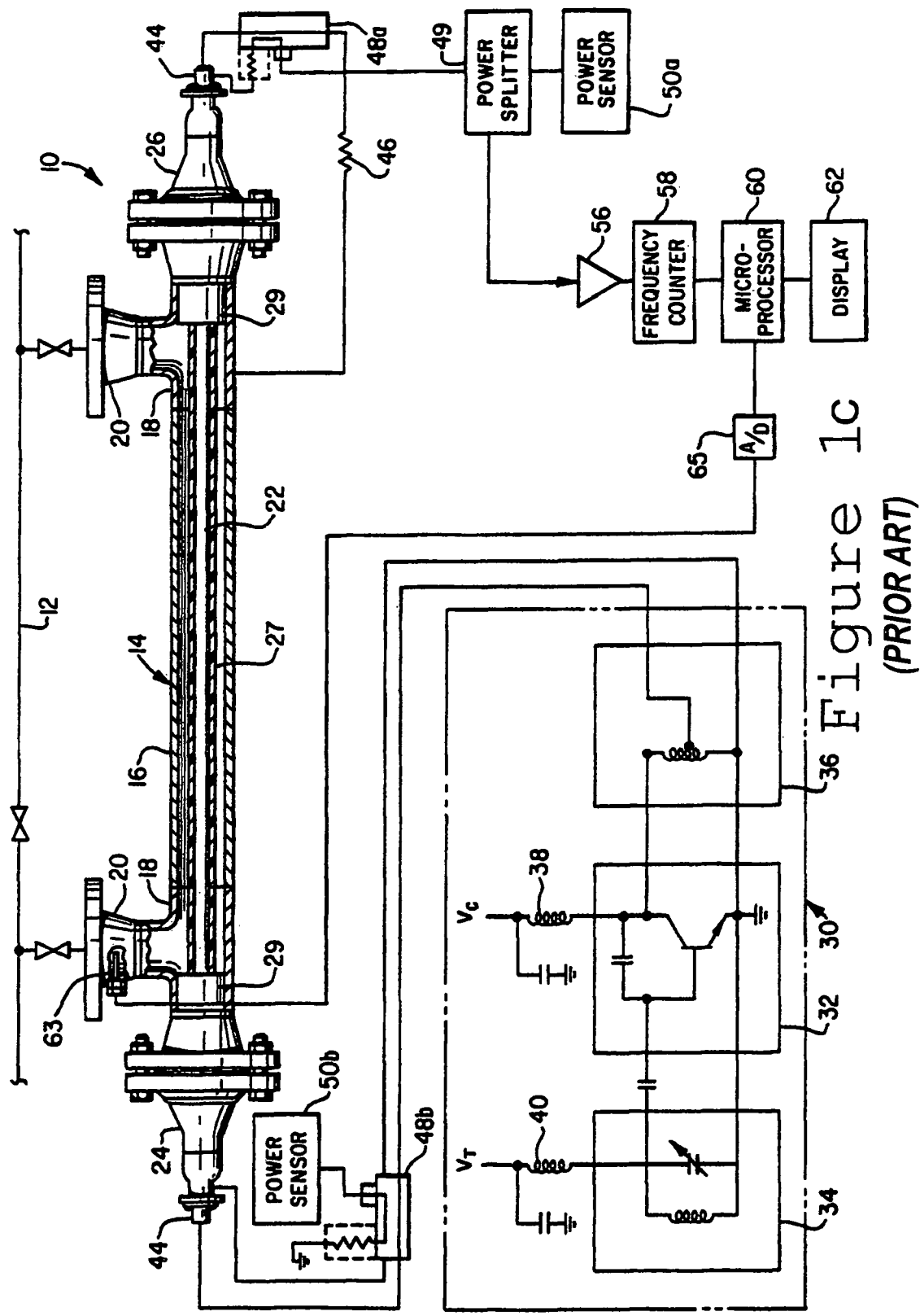
FIG. 1C shows a reproduction of U.S. Pat. No. 4,996,490 FIG. 1A as an example of one embodiment of the present innovations of an electromagnetic characterization analyzer that can perform a water-cut analysis on a multiphase fluid flow stream.

Water-cut electromagnetic characterization analyzers can perform the function of water-cut measurement in component 590. U.S. Pat. No. 4,996,490 describes preferred some of the preferred embodiments of water-cut electromagnetic characterization analyzers to be used in the present application. FIG. 1C is a reproduction of FIG. 1A from U.S. Pat. No. 4,996,490 as an example of one embodiment of the present innovations of an electromagnetic characterization analyzer that can be used with the present innovations. Specifically, FIG. 1C shows illustrated a diagram of an apparatus for measuring the concentration of one substance or material such as water, in another substance or material such as crude petroleum oil, which is being transmitted as a liquid mixture flow stream through a pipeline. The apparatus is generally designated by the numeral 10 and is particularly adapted for interconnection with a fluid transmission pipeline 12 for sampling the pipeline flow stream. Alternatively, the apparatus 10 might become part of the pipeline. The apparatus 10 includes a fluid flow conducting and measurement section 14 comprising an outer conduit section 16, including spaced apart pipe tee sections 18 having conventional flange portions 20 formed thereon for connection to branch conduit portions of the pipeline 12. The measurement 14 comprises a coaxial transmission line which includes a center conductor 22 preferably formed of a metal such as stainless steel which extends between opposed end support parts 24 and 26 which are described in detail in the above-referenced patent application. The center conductor 22 preferably comprises a generally cylindrical rod or tube member coaxially arranged in the conduit 16 and provided with an outer sheath 27 formed of a material having a relatively low dielectric loss tangent, preferably less than 0.1 at a frequency of 1.0 GHz. The sheath 27 preferably comprises a relatively easy-to-fabricate plastic such as polypropylene, a plastic sold under the trademark Delrin or one of the fluorocarbon plastics. Alternatively, certain ceramics or other materials may also be used as the outer sheath 27 as long as they are low loss tangent dielectric materials. The fit between the outer sheath 27 and the center conductor 22 is preferably a forced or line-to-line fit although some clearance may be permitted as long as fluid flow between the center conductor and the outer sheath is prohibited. In an apparatus where the center conductor has a diameter of 0.25 inches, the outer diameter of the sheath 27 is preferably at least about 0.50 inches or, alternatively, a ratio of the outer diameter of the sheath to the outer diameter of the center conductor is in the range of about two to one.

It has been determined that with the provision of a sheath 27 formed of one of the above-mentioned materials and in the proportions described, that the electrical circuit for propagating microwave radiation through the apparatus 22 retains a high quality signal resolution characteristic in liquid mixtures of oil and water, for example, wherein the water content is relatively high, that is on the order of more than 5% to 10% by volume. With this type of center conductor arrangement, the circuit associated with the apparatus 10 and described herein below retains good field intensity or prevents short circuiting of the center conductor to the outer conductor in an unwanted location, the oscillator circuit retains its good load-pulling characteristics with good resolution of phase and the interface between the sheath 27 and the fluid in the conduit 16 is a new propagation medium which has desirable operating characteristics.

When the apparatus 10 is operating with a liquid composition which is high in water content or a so-called water continuous phase, the conductivity of the composition is high compared to a good dielectric but low compared to a good conductor and, of course, the liquid composition is in direct contact with the wall surfaces of the measurement section 14 including the center conductor. The insulating sheath 27 prevents the radio frequency (RF) energy (e.g. microwave energy) from being shorted out immediately at the point where the RF energy enters the measurement section or where the fluid cross section begins. Moreover, the sheath 27 now becomes the primary region where the RF field is propagated with the conductive fluid becoming a pseudo outer wall of the measurement section in place of the wall of the conduit 16. The cross sectional measurement of the water-in-oil composition is still preserved due to the large skin depth of the microwave or RF energy at the operating frequency. This skin depth is large through the water as the conducting medium of the outer half of the coaxial transmission line formed by the measurement section. The dielectric structure is now the sheath 27. The properties of the propagated RF energy still reflect the changing content of the oil in the water and this is related through pulling of the unisolated oscillator which is described herein below. The sheath 27 must be thick enough to maintain a reasonable coaxial impedance to be able to propagate the RF energy into the measurement section 14 and maintain a measurement capability. A very thin dielectric coating on the center conductor 22 will cause very low impedance with a liquid composition having a high water content and therefore the RF energy would be reflected at the fluid interface.

RF energy is not propagated in the interior of a good conductor. The conductor guides the electromagnetic waves. The energy travels in the region between the conductors in a coaxial transmission system with a good dielectric. The currents that are established at the conductor surfaces propagate into the conductor in a direction perpendicular to the direction of the current density. The current density or electric field intensity established at the surface of a good conductor decays rapidly looking into the conductor. When the conductor is resistive or, low conductivity, this depth into the conductor increases rapidly. This phenomenon is known in the art as skin depth.

As shown in FIG. 1C, the center conductor 22 extends through opposed end block members 29 which are also preferably formed of a relatively high insulative material such as a fluorocarbon plastic and the end plug sections are configured in a way similar to the ones described in the above-referenced patent application.

The measurement section 14 is operably connected to a source of radio frequency (RF) or so-called microwave energy comprising an unbuffered or unisolated, free-running oscillator, generally designated by the numeral 30. The oscillator 30 includes an active circuit 32 operably connected to a tuning circuit 34 and to an impedance matching network circuit 36. The circuit 32 is adapted to receive a constant DC voltage, $V_c$, from a source not shown and by way of a filter circuit 38. The tuning circuit 34 is also adapted to receive a controllable DC voltage, $V_t$, from another source, not shown, by way of a second filter circuit 40. The oscillator 30 has an appreciable load-pulling characteristic. The fundamental operating frequency of the oscillator is changed as the complex load is changed on the output circuit of the oscillator. The oscillator 30 is preferably of a type commercially available such as from Avantek Company, Santa Clara, Calif. as their model VTO 8030 voltage controlled oscillator. The exemplary oscillator 30 has a maximum load-pulling characteristic of about 35 MHz at a nominal 200 MHz operating frequency into all phases of a short circuit at the end of a 50 Ohm line stretcher (approximately 0.5 DB return loss). The oscillator 30 is operably connected to the apparatus measurement section 14 through a suitable connector 44 which is in electrically conductive engagement with the center conductor 22 at the end part 24 and at the opposite end of the center conductor 22 through a second connector 44, a resistance 46 and with the outer conductor or conduit 16 as illustrated. The end part 26 is also adapted to connect the center conductor 22 with a 10 DB directional coupler 48a which is operable to sample the microwave energy or power transmitted through the coaxial measurement section 14. The coupler 48a is connected to a power splitter 49 which is connected to a power sensor 50a. The directional coupler 48a may be of a type manufactured by Minicircuits Company of Brooklyn, N.Y. as their model ZED-15-2B. The power splitter 49 may be of a type ZFSC-2-2 also manufactured by Minicircuits. The power sensor 50 may be of a type 437B manufactured by Hewlett Packard of Sunnyvale, Calif.

A second directional coupler 48b is interposed in the circuit between the end part 24 and the oscillator 30 and is connected to a second power sensor 50b. The directional couplers 48a and 48b may be of identical configuration. The coupler 48a is connected to the power splitter 49 which provides an output signal which is amplified by an amplifier 56. The output of the amplifier 56 is adapted to be input to a frequency counter 58 which is also adapted to be connected to a microprocessor 60. A suitable digital display or readout device 62 is connected to the microprocessor 60. The amplifier 56 may be of a type commercially available from the above-mentioned Minicircuits Company as their model ZFL-500. The frequency counter 58 may be of a type manufactured by Hewlett Packard Company as their model 5342A and the microprocessor 60 may be a Hewlett Packard type 9836. The system illustrated in FIG. 5 preferably includes a temperature compensation circuit including a thermocouple 63 operably connected to a conversion circuit 65 to provide a suitable digital signal to the microprocessor 60.

In operation, the changing dielectric constant presented by the material flowing through the measurement section 14, such as caused by the presence in a liquid mixture, for example, of varying amounts of water in oil or oil in water, causes the oscillator 30 to change its operating frequency over a relatively narrow frequency band as compared with the nominal operating frequency of the oscillator. For example, the oscillator 30, in a preferred form, can be pulled from its nominal operating frequency through a range of about 20 MHz by the changing dielectric constant of the medium flowing through the measurement section 14.

Figure 2:
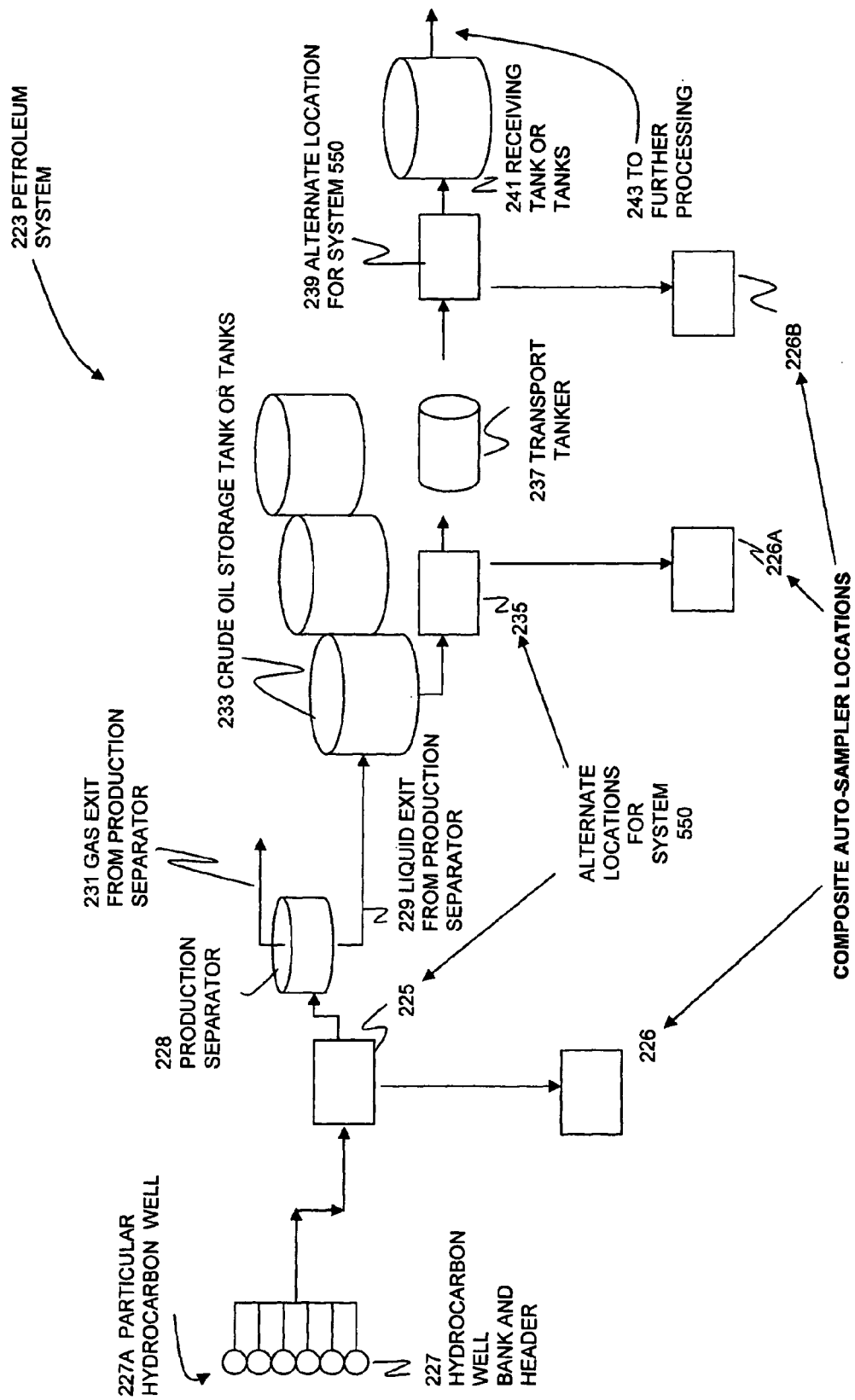
FIG. 2 shows an exemplary petroleum processing and transportation system, including wells, a pipeline, a pipeline header, a storage tank prior to transport, a transport tanker, and a receiving storage tank in which the multiphase fluid characterization apparatus from FIG. 5 is incorporated at various locations, consistent with a preferred embodiment.
Figure 3:
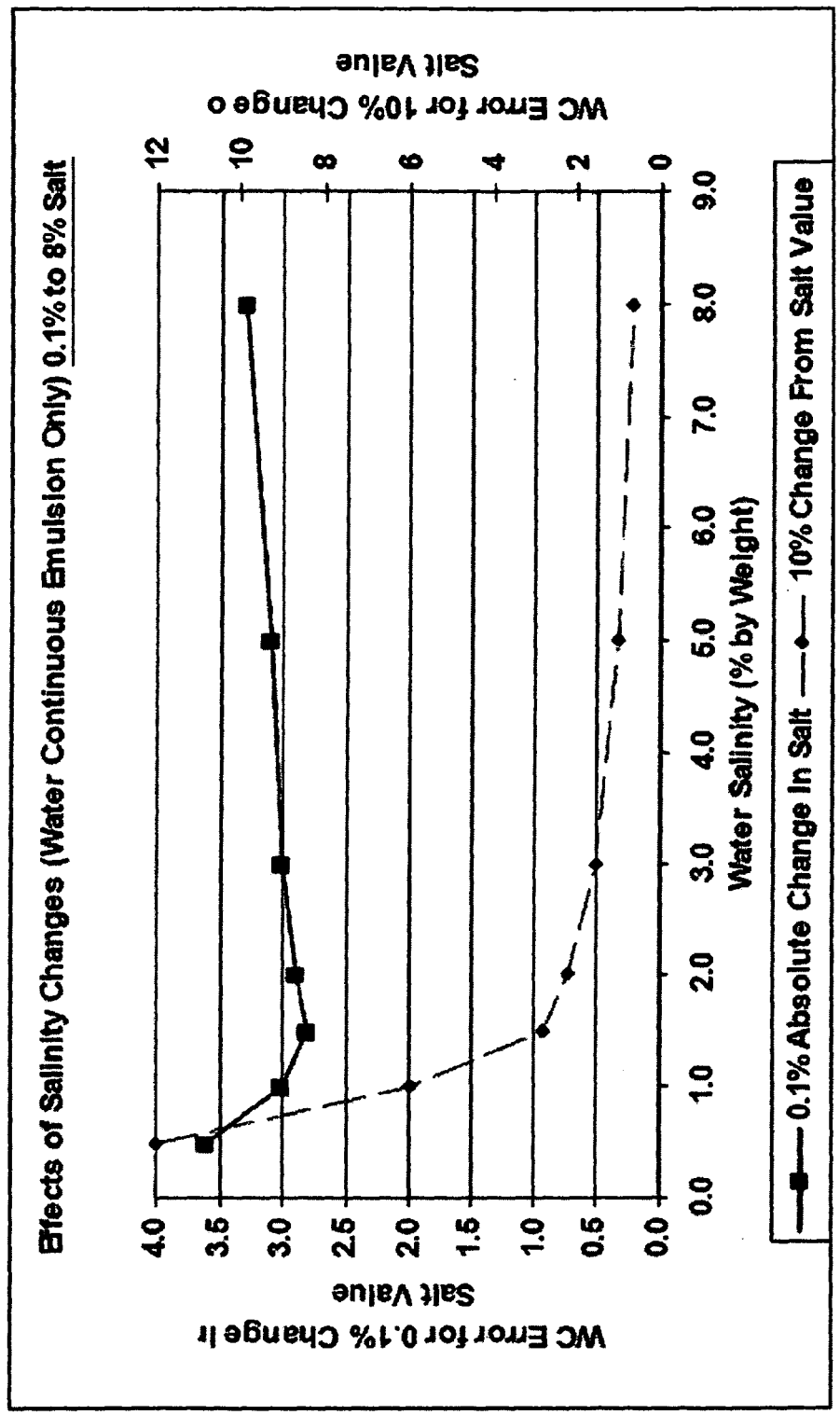
FIG. 3 shows exemplary electromagnetic characterization analyzer water cut salinity correction offsets for a generally low range of salinity, of about 0.1% to 8% salinity, as previously described.
Figure 4:
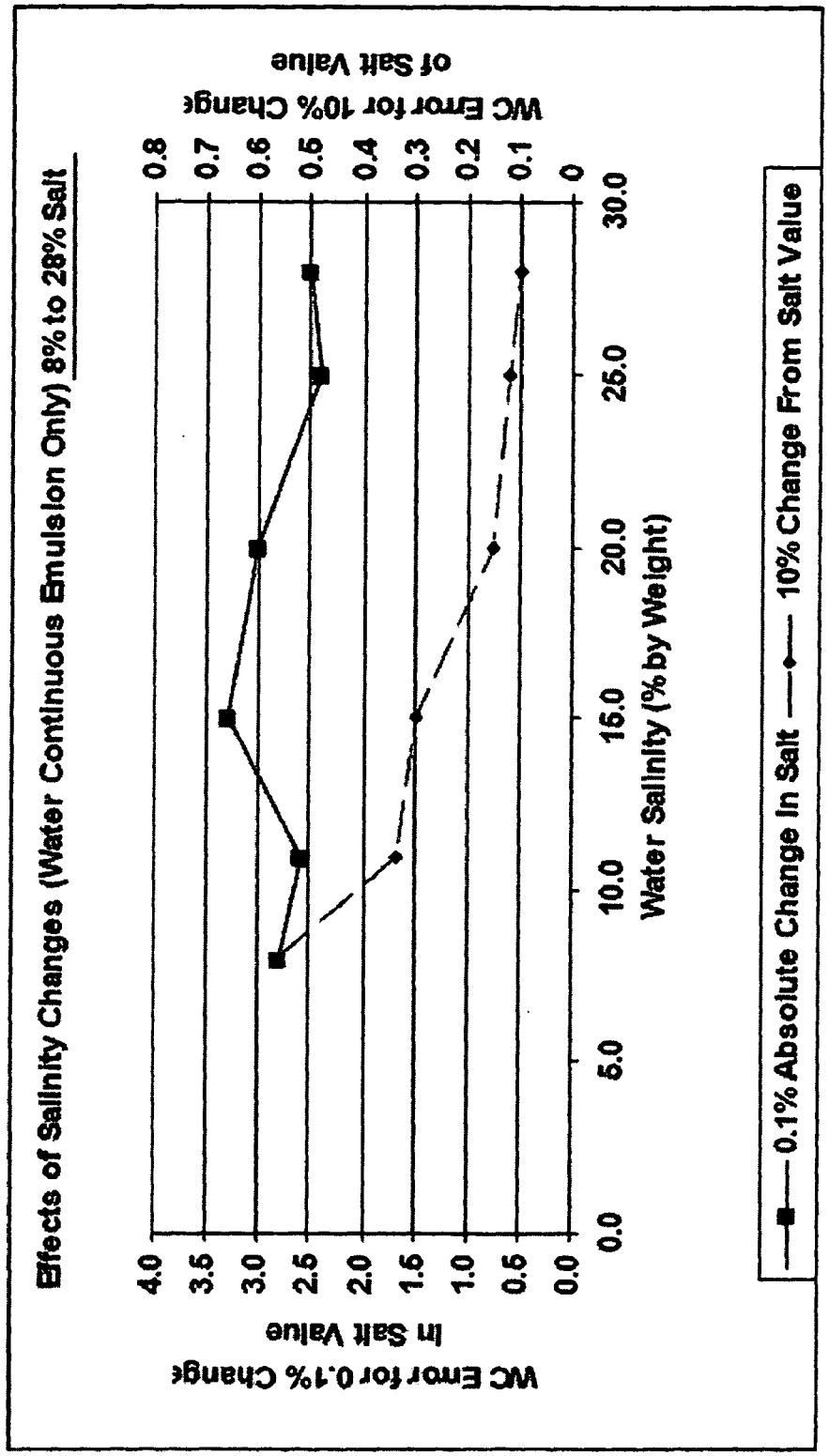
FIG. 4 shows exemplary electromagnetic characterization analyzer water cut salinity correction offsets for a generally high range of salinity, of about 8% to about 28% salinity, as previously described.

FIG. 2 shows a petroleum processing, characterization, and transportation system 223 according to an illustrative, non-limiting embodiment consistent with the present application in which a multiphase fluid characterization apparatus 550 can be incorporated at numerous points, depending on the desired characterization. The pipeline leads from a set of petroleum-producing wells 227 or a given well 227A which all or some may be located on land or under-sea. The multiphase fluid characterization apparatus 550 is usually placed at point 225. This can be close to the wellhead, for example, or further down the pipeline leading from the wellhead. In the case of off-shore hydrocarbon wells, it may alternatively be performed on an offshore platform or a floating production ship. The multiphase fluid characterization apparatus 550 may be positioned between wells 227 and an oil-water separator 228, which is upstream of a storage tank 233. Stream 229 represents the separated water phase leaving the oil-water separator 228 whereas stream 231 is the separated gas leaving the separator. The contents of storage tank 233 can optionally be loaded into transport tanker 237 which can be unloaded from the transport tanker 237 to receiving storage tank 241. The multiphase fluid characterization apparatus 550 can also be place at 235 or 239 to characterize the petroleum as it is either loaded and/or unloaded from a shipping tanker.

FIG. 1A shows method 100 according to one embodiment of the disclosed innovations for improving on-line analyzer measurements and characterization of the content or percentage of a first component in a multiphase fluid. In one embodiment of the present innovations, known values are inputted for use in the development of corrective transforms by computer or microprocessor system 572 (step 102). In another embodiment, the length of the test time is entered (step 102). In one embodiment of the present innovations, the method of FIG. 1A requires that electrical properties of the multiphase fluid be read and collected (step 104). In one embodiment of the present innovations, the method of FIG. 1A requires that non-electrical properties of the multiphase fluid be read and collected (step 106). All of these values may then be collected or stored in the memory of the computer or microprocessor system 572 and then be used to implement methods, such as the method of FIG. 1A. In one embodiment of the present innovations, the values can also be communicated to an external system 574 via link 596 for various operations such as storage, processing, data manipulation, transform development, and correction of raw data via the transforms by implementing the method of FIG. 1A on external system 574. In one embodiment of the present innovations in which the length of a test is inputted, the method checks to see if the test and gathering of data is complete (step 108). If not, the method repeats, or "loops", by returning to step 104 to collect more measurement values. Then, in one embodiment of the present innovations, at the end of, for example, a well production period, as decided by step 108, the method identifies extrema such as minima and maxima, or groups of minima and maxima, or groups of values within boundaries of a particular phase, in the property measurements (step 110). In one embodiment of the present innovations, the method then derives corrective transforms (step 112). In one embodiment of the present innovations, the method then applies the corrective transforms to measurements (step 114). In one embodiment of the present innovations, a decision is then made as to whether the method needs to further refine the corrective transforms. (step 116). If so, another test period can be run to gather more data by returning to step 104. If not, the corrected data is outputted (step 118), which, in one embodiment of the present innovations, includes corrected electrical property characterizations. In one embodiment of the present innovations, flow weighted averages for the water-cut are calculated, stored, and displayed.

Figure 6:
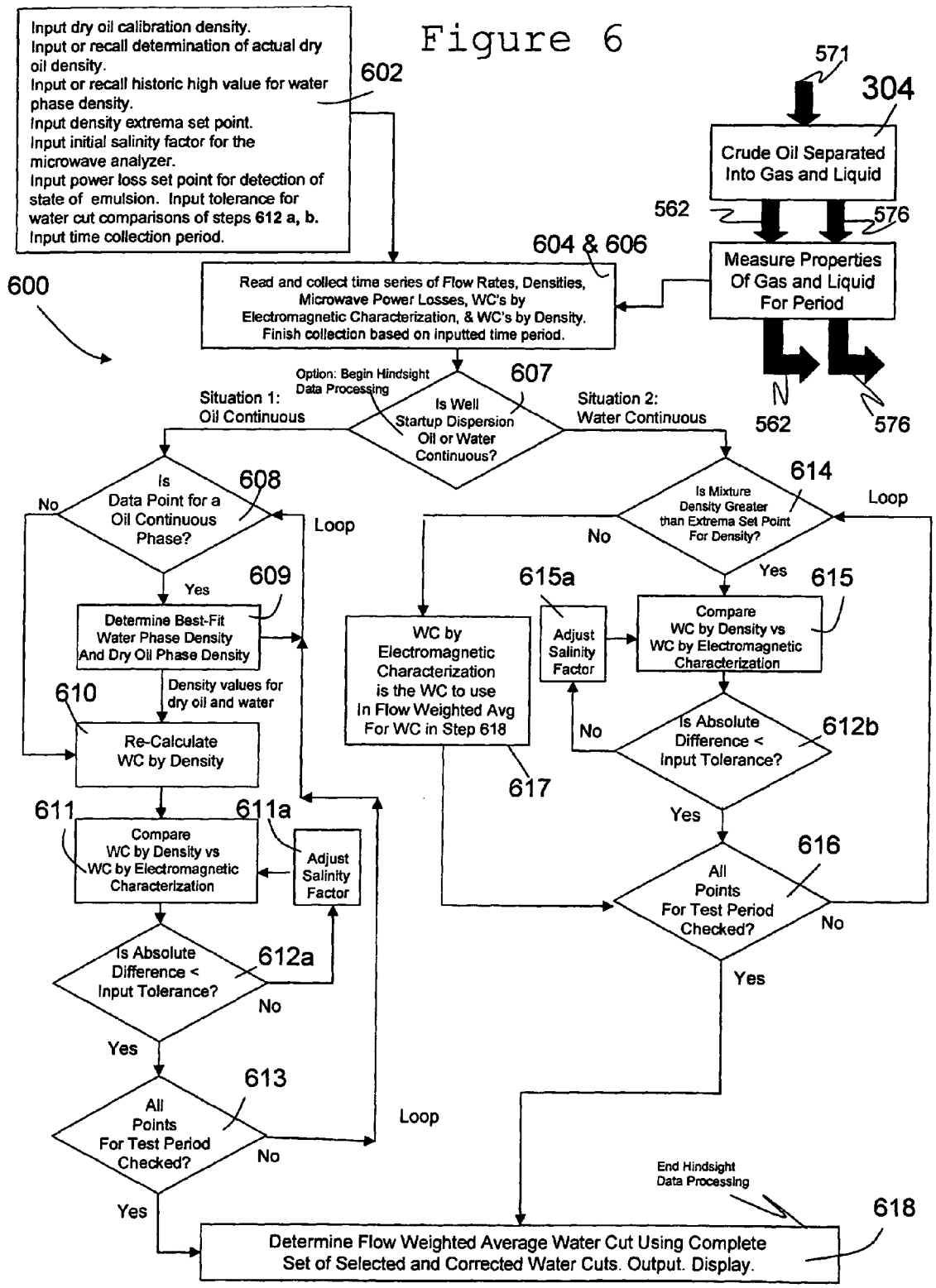
FIG. 6 shows one embodiment of the present innovations to correct for salinity-dependent uncertainties when an electromagnetic characterization analyzer is measuring a multiphase fluid in which water can be the continuous phase as occurs during production from a high water-cut hydrocarbon well.

FIG. 6 shows method 600 according to a preferred embodiment of the disclosed innovations for improving on-line water-cut measurements on crude oil emerging from a hydrocarbon well. In one embodiment of the present innovations, the method of FIG. 6 receives: (1) an input of the dry oil calibration density for use in correcting an electromagnetic characterization analyzer for shifts in actual dry oil density from the calibration dry oil density as disclosed in Scott '613, (2) an input of the actual, estimated, or determined dry oil density characteristic of the particular well or field or fields from which the well draws from, (3) an input of the actual water phase density or historic high value water phase density, (4) an input of the set point for density extrema identification, (5) an input for an initial salinity factor for the electromagnetic characterization analyzer, (6) an input power loss set point for detection of the state of the emulsion or dispersion according to the Scott '490 patent, (7) an input tolerance for water-cut comparisons between the water-cut by electromagnetic characterization and the water-cut by density, and (8) a time period for collecting the measurements (step 602). In one embodiment of the present innovations, the method of FIG. 6 requires that on-line electromagnetic characterization analyzer 590 electrical measurements of water cut by electromagnetic characterization and microwave power loss factors for phase state detection be read and collected (step 604) on liquid stream 576. In one embodiment of the present innovations, densitometer 592 makes measurements on liquid stream 576, including the mixture density and the flow rates of stream 576. These measurements are made and collected (step 606). In one embodiment of the present innovations, all of these values may then be collected and stored in the memory of the computer or microprocessor system 572 or external system 574 and then be used to implement methods, such as the further steps of the method of FIG. 6. In one embodiment of the present innovations, the values can also be communicated to an external system 574 via link 596 for various operations such as storage, processing, data manipulation, transform development, and correction of raw data via the transforms by implementing the further steps of method of FIG. 6 on external system 574. In one embodiment of the present innovations, the method of FIG. 6 calculates the water-cut by density in step 606. In one embodiment of the present innovations, the method of FIG. 6 completes the collection of the measurements in steps 604 and 606 for the time period inputted in step 602.

In one embodiment of the present innovations, the method of FIG. 6 then begins a hindsight processing of the data collected in steps 604 and 606, beginning with step 607. In one embodiment of the present innovations, step 607 determines if the particular that has been tested started-up during the test as an oil-continuous dispersion or a water-continuous dispersion.

In one embodiment of the present innovations, a first situation is considered if the start-up dispersion is found to be oil-continuous per step 607. In one embodiment of the present innovations, a data processing loop begins in step 608. In one embodiment of the present innovations, step 608 checks the first data point to determine if the dispersion is oil-continuous using the inputted power loss set point as inputted in step 602. In one embodiment of the present innovations, if the dispersion or emulsion is oil-continuous per step 608, step 609 performs a best-fit determination for the oil-free water phase density and the dry oil phase density using at least two oil-continuous time series data points. In one embodiment of the present innovations, step 609 then loops back to step 608 and checks the next time series data point. In one embodiment of the present innovations, if step 608 finds the particular time series data point is not oil-continuous but is water-continuous, step 610 then recalculates the water-cut by density for that particular time series data point. In one embodiment of the present innovations, step 610 uses a water phase density as inputted in step 602, an oil phase density as inputted in step 602, the water cut by electromagnetic characterization for that time series data point as determined in step 604, and a mixture density as determined in step 606. In one embodiment of the present innovations, step 610 recalculates the water-cut by density for that data point by using the best fit oil and water densities from step 609, the water cut by electromagnetic characterization for that time series data point as determined in step 604, and a mixture density as determined in step 606. In one embodiment of the present innovations, step 611 compares the recalculated water-cut by density from step 610 to the water-cut by electromagnetic characterization from step 604. In one embodiment of the present innovations, step 612a then determines if the absolute difference between the two water-cuts is less than the tolerance inputted in step 602. In one embodiment of the present innovations, if the difference is not less than the inputted tolerance, then the salinity factor for the electromagnetic characterization analyzer is adjusted in step 611a (from the initial salinity factor inputted in step 602), to converge the water-cut by electromagnetic characterization to within the inputted tolerance of the water-cut by density for that particular data point. In one embodiment of the present innovations, if the difference is within the tolerance, step 613 checks to determine if all data points in the time series have been processed. In one embodiment of the present innovations, if all data points have not been processed, the method loops back to step 608 to check the next or remaining data point through the process just described. In one embodiment of the present innovations, once step 613 determines all data points have been processed, the complete set of data points for the times series, including the water-cut by electromagnetic characterization for the oil continuous data points and the corrected water-cut by densities for the water continuous data points is outputted to step 618 to calculate, store, output, and/or display a flow weighted averages for the water cut.

In one embodiment of the present innovations, a second situation is considered if the start-up dispersion is found to be water-continuous per step 607. In one embodiment of the present innovations, a data processing loop begins in step 614. In one embodiment of the present innovations, step 614 checks the first data point to determine if the mixture density read in step 606 for that data point in the time series has a density greater than the density extrema set point entered in step 602. In one embodiment of the present innovations, if step 614 finds the mixture density is less than the set point, then the water-cut by electromagnetic characterization is chosen in step 617 as the better value for the water-cut as compared to the water-cut by density. In one embodiment of the present innovations, if step 614 finds the set point is exceeded, then step 615 compares the water-cut by density from step 606, where the water-cut by density was calculated using the historical high value for the water phase density, as inputted or recalled in step 602, to the water-cut by electromagnetic characterization from step 604 for that data point. In one embodiment of the present innovations, step 612b determines if the absolute difference between the two water-cuts is less than the tolerance inputted in step 602. In one embodiment of the present innovations, if the difference is not less than the inputted tolerance, then the salinity factor for the electromagnetic characterization analyzer is adjusted in step 615a (from the initial salinity factor inputted in step 602), to converge the water-cut by electromagnetic characterization to within the inputted tolerance of the water-cut by density for that particular data point in the time series. In one embodiment of the present innovations, if the difference is within the tolerance, step 616 checks to determine if all data points in the time series have been processed. In one embodiment of the present innovations, if all data points have not been processed, the method loops back to step 614 to check the next or remaining data point through the process just described. In one embodiment of the present innovations, once step 616 determines all data points have been processed, the complete set of data points for the times series, including the water-cut by electromagnetic characterization for the data points whose mixture density is less than the set point as determined in step in 614 and selected as the best water cut value in step 617, the water-cut by densities for the water continuous data points is outputted to step 618 to calculate, store, output, and/or display a flow weighted averages for the water cut.

In one embodiment, 1000 kg/m$^3$ is the set point inputted in step 602 to check the mixture density against for wells that start-up as water-continuous dispersions.

In one embodiment, the multiphase fluid may be petroleum produced by a well as shown in FIG. 2. The petroleum may be a liquid stream comprising oil and a water phase. A hydrocarbon gas also produced by the well may have been previously separated from the liquid stream.

In one embodiment, the accuracy of the characterization of multiphase fluid mixtures can be improved using some of the benefits of the present innovations, and further improved using all of the benefits of the present invention.

According to a disclosed class of innovative embodiments, there is provided a method for determining a first phase fraction in a multiphase fluid flow stream, comprising the actions of (a) collecting a time series of measurements of the multiphase fluid, (b) selecting ones of measurements of said time series by applying a pre-determined selection criterion to at least a first said property, (c) deriving at least one corrective transform in at least partial dependence on the results of said action (b), (d) applying said corrective transform to ones of said time series of measurements, and (e) using the results of said action (d) to calculate the fraction of the first phase in the multiphase fluid.

According to a disclosed class of innovative embodiments, there is provided a method for determining a first phase fraction in a multiphase fluid flow stream, comprising the actions of (a) collecting a time series of measurements of at least a first and a second property of said multiphase fluid, (b) finding ones of measurements of said first property in said time series meeting pre-determined extremal condition selection criteria, (c) deriving at least one corrective transform from said extrema, (d) applying said corrective transform to measurements of said second property in said time series, and (e) calculating the fraction of the first phase in the multiphase fluid in accordance with said action (d).

According to a disclosed class of innovative embodiments, there is provided a method for determining the water cut of a multiphase stream, comprising the actions of (a) collecting a time series of measurements of the multiphase fluid, (b) selecting ones of measurements of said time series meeting pre-determined extremal condition selection criteria, (c) based on the results of said action (b), wherein said action (c) deriving a corrected estimate of dry oil density from at least one oil-continuous measurement, and/or deriving a corrected estimate of aqueous salinity from at least one water-continuous measurement, and (d) using said corrected estimates to estimate water-cut.

According to a disclosed class of innovative embodiments, there is provided a method for measuring mixtures of multiple fluids, comprising the actions of (a) measuring one or more electrical properties of a fluid, measuring one or more non-electrical physical properties of a fluid, and collecting a time series of measurements produced thereby, (b) determining extreme values of said measurements, and (c) determining correct fluid properties based not only on said time series of measurements but also on correcting factors determined from said extreme values.

According to a disclosed class of innovative embodiments, there is provided a multiphase fluid characterization system comprising a component which measures the density of a multiphase fluid flow stream, a component which measures the one or more electrical properties of said fluid flow stream, and a system which collects a time series of measurements produced by said components, determines ones of said measurements meeting pre-determined extremal condition selection criteria, and determines correct fluid properties based not only on said time series of measurements but also on correcting factors determined from said extreme values.

Modifications and Variations

As will be recognized by those skilled in the art, the innovative concepts described in the present application can be modified and varied over a range of applications, and accordingly the scope of patented subject matter is not limited by any of the specific exemplary teachings given. It is intended to embrace all such alternatives, modifications and variations that fall within the spirit and broad scope of the appended claims.

The methods and systems of the present application can operate across a wide range of processing situations and conditions. One of ordinary skill in the art, with the benefit of this disclosure, will recognize the appropriate use of the methods and systems for a chosen application of a given or dynamic set of operating parameters, including process pressure, process temperature, process flow rate, multiphase fluid composition, aqueous phase composition, non-aqueous-phase composition, presence of condensible gases, presence of non-condensible gases, use of flow stream conditioning operations prior to characterization, flow stream pipe location, slip-stream installation versus full-stream installation versus insertion installation, characterization apparatus location, ambient temperature, or other conditions.

Optionally, the methods and systems of the present application can be configured or combined in various schemes. The combination or configuration depends partially on the required measuring precision and accuracy and the operational envelope of the process. One of ordinary skill in the art, with the benefit of this disclosure, will recognize the appropriate combination or configuration for a chosen application.

Optionally, the methods and systems of the present application may also take the temperature and pressure of the multiphase fluid in streams 552, 572, 562, 576, and 580, the density of a gas stream in stream 562, the liquid level in separator 560, and any flags such as separator level out of range which may define the reliability of the data or provide variables to use for analysis. One of ordinary skill in the art, with the benefit of this disclosure, will recognize the appropriate additional measurements that would be beneficial for a chosen application. Optionally, such measurements taken by the methods and systems of the present application may also be sent to the external computer or microprocessor system 174 for processing. For example, if the gas density exceeds a certain amount, this fact could be used to flag improper data due to liquids carrying over into the gas from the separator during a system upset. Liquid density having a large standard deviation beyond a preset level might be used for the same determination. This would be due to gas carry under into the liquids, which would make the liquid density very noisy.

Optionally, multiphase fluid temperature compensation can be employed used to adjust for shifts in temperature using reference data sets relating temperature change to total fluid density change, or curves fitted to such reference data. Optionally, because the thermal expansion of an oil continuous dispersion is generally different than the thermal expansion of a water-continuous dispersion, different reference data sets or curves fitted to such data sets may be employed. Optionally, because the coefficient of thermal expansion for aqueous solutions and non-aqueous solutions differ, calculation routines can use the measured first phase fraction to better adjust for such temperature shifts. One of ordinary skill in the art, with the benefit of this disclosure, will recognize the appropriate systems to employ for such temperature compensation methods.

Optionally, methods such as the method of FIG. 1A or FIG. 6 could include a cross-check step for incorrect phase state detection by the electromagnetic characterization analyzer 590 using water cut by density values from the densitometer 592. Specifically, if the meter 590 chose the wrong phase state and calculated a water-cut by electromagnetic characterization, of say, 40%, and densitometer 592 calculated a water-cut by density of say 85%, it is likely that, for some unknown or spurious condition, the electromagnetic characterization analyzer chose the wrong phase state and that particular data point could be recalculated using the other phase as the basis for the re-calculation. Appropriate routines could be worked into method such as the method of FIG. 1A or 6 to account for this situation.

Optionally, methods such as the methods of FIG. 1A or FIG. 6 could include a subroutine incorporating the disclosure or teaching of Scott '613 to account for uncertainties in oil-continuous dispersions of less than about 5% water-cut.

Optionally, methods such as the methods of FIG. 1A or FIG. 6 could include a subroutine incorporating the disclosure or teaching of Scott '613 to adjust for shifts in the actual dry oil density away from the calibration dry oil density.

Optionally, examples of suitable hardware which can be fully or partially modified to fully or partially embody the methods and systems of the present application include those that are commercially available from Phase Dynamics of Richardson, Texas, under the name known to the industry as Compact Cyclone Multiphase Meter ("CCM").

Optionally, the systems of the present application may not be located in a pipe or conduit. In one class of embodiments, the physical property measuring component and the electrical property measuring component may be located via an insertion installation in a vessel such as a storage tank, mixing tank, accumulator, separator, liquid-liquid contactor, or other processing device for which a multiphase fluid characterization is required. One of ordinary skill in the art, with the benefit of this disclosure, will recognize the appropriateness of the methods and systems of the present application for a chosen application.

Optionally, the systems of the present application can include a sampling port for comparison of the on-line determinations of first phase with an off-line determination.

Optionally, the extrema pre-determined selection criterion of the methods of the present application may not only be predetermined values of particular measurements or calculations to trigger selection of extrema, but the criterion may be a sub-routine of equations, comparisons, noise reduction, or other data manipulation techniques. One of ordinary skill in the art of data manipulation, with the benefit of this disclosure, will recognize the appropriateness of such sub-routine options.

Optionally, selection of the extrema can be conditioned by excluding measurements too close in time to a start point.

Optionally, the methods of the present application can also be embodied in a set of instructions that can be used on a general purpose desktop or laptop computer or microprocessor system, such as external system 574. The set of instructions can comprise input instructions that receives data from flow computer or microprocessor system 572. Similarly, the input instructions can accept instructions from a user via one or more input devices, such as a keyboard, mouse, touchpad, or other input device. The instructions can also implement the methods of the present invention or any part thereof to generate, for example, an updated transform for the calculation of first phase fraction by either the density method or the electromagnetic characterization method. The instructions can cause the computer or microprocessor system to display information, such as the results of the methods of the present invention, to a user, through a display monitor, printer, generated electronic file, or other such device. The instructions can also cause the computer or microprocessor system to transmit the results to a distant user via modem, cable, satellite, cell link, or other such means. For such digital communications, RS-422 or RS-485 can optionally be used to allow links from flow computer or microprocessor system 572 or external system 574 to multiple external units. Optionally, a 4-20 milliamp analog output signal can be used to allow external processing of the system measurements.

Optionally, the methods of the present invention can also be embodied in a computer readable medium.

The present application frequently refers to "microwave" measurements for electromagnetic characterization which uses a baseline oscillator frequency in the VHF or UHF range. However, this term is used merely for convenience, and a variety of frequencies and methods can be used for electromagnetic characterization.

The preferred embodiment uses frequency measurement of a load-pulled oscillator to achieve electromagnetic characterization of a fluid flow which has some electromagnetic coupling to the oscillator's feedback path. This embodiment is particularly preferable, due to the sensitivity and rapid response of load-pulled measurement systems. However, it should be noted that many of the disclosed inventions can also (alternatively and less preferably) be applied to many other kinds of electromagnetic characterization systems.

Additional general background, which helps to show variations and implementations, may be found in the following publications, all of which are hereby incorporated by reference: Bentley N. Scott, Larry Baker, and Dr. Bjornar Svingen, $16^{th}$ North Sea Flow Measurement Workshop 1998, "Well Testing Issues and a New Compact Cyclone System;" Compact Cyclone Multiphase Meter (CCM) Specifications Sheet, CCM Literature 0205, available on the Web, (as of the filing date of this application); and "Family of Water Cut Analyzers, Analyzer Family 0306," available on the Web (as of the filing date of this application).

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A method for determining a first phase fraction in a multiphase fluid flow stream, comprising the actions of:
   a) collecting a time series of measurements of the density and at least one electrical property of the multiphase fluid;
   b) selecting density extrema of said time series by applying a pre-determined selection criterion to at least said density measurements;
   c) deriving at least one corrective transform in at least partial dependence on the results of said action (b);
   d) applying said corrective transform to ones of said time series of said electrical property measurements; and
   e) using the results of said action (d) to calculate the fraction of the first phase in the multiphase fluid.

2. The method of claim 1, wherein said action (c) derives said corrective transform by calculating a first phase fraction by the density method for said ones of measurements meeting the extremal condition selection criteria, using those calculated first phase fractions to derive new values for the permittivities of the first and second phases, and using those new permittivity values for calculating corrected first phase fractions by the electromagnetic characterization method.

3. The method of claim 1, wherein said action (c) derives said corrective transform by calculating new values for the assumed aqueous phase densities and non aqueous phase densities.

4. The method of claim 1, wherein said step (b) is performed in hindsight.

5. The method of claim 1, wherein said step (b) is performed in hindsight on at least some data which is at least tens of minutes old.

6. The method of claim 1, wherein said corrective transform is updated as said time series measurements are obtained and as said ones of measurements meeting said extremal condition selection criteria are determined.

7. The method of claim 1, further comprising integrating the results of said action (e) to produce a resulting quantity estimate.

8. The method of claim 1, wherein the multiphase fluid is petroleum, and said first phase is an aqueous phase.

9. The method of claim 1, wherein said times series comprises measurements of electrical properties selected from the group consisting electrical measurements corresponding to permittivity, electromagnetic power loss measurements, and flow rate measurements of said multiphase fluid.

10. The method of claim 1, wherein said measurements are at least partly determined from calculations.

11. The method of claim 1, wherein said action (e) is also at least partially based on historical data.

12. The method of claim 1, wherein points of said time series are not equally spaced in time.

13. The method of claim 1, further comprising the additional step of filtering said time series.

14. The method of claim 1, further comprising the additional step of decimating said time series.

15. The method of claim 1, wherein gases are essentially removed prior to conducting the time series of measurements.

16. A method for determining a first phase fraction in a multiphase fluid flow stream, comprising the actions of:
   a) collecting a time series of measurements of the density and at least one electrical property of said multiphase fluid;
   b) finding extrema of the density of said fluid in said time series meeting pre-determined extremal condition selection criteria;
   c) deriving at least one corrective transform from said extrema;
   d) applying said corrective transform to ones of said electrical property measurements in said time series; and
   e) calculating the fraction of the first phase in the multiphase fluid in accordance with said action (d).

17. The method of claim 16, wherein said times series comprises measurements selected from the group consisting of density, electrical measurements corresponding to permittivity, electromagnetic power loss measurements, and flow rate measurements of said multiphase fluid.

18. The method of claim 16, wherein said step (b) is performed in hindsight.

19. The method of claim 16, wherein said step (b) is performed in hindsight on at least some data which is at least tens of minutes old.

20. A method for determining the water cut of a multiphase stream, comprising the actions of:
   a) collecting a time series of measurements of the density and at least one electrical property of the multiphase fluid;
   b) selecting ones of measurements of said time series meeting pre-determined density extremal condition selection criteria;
   c) based on the results of said action (b),
      i) deriving a corrected estimate of dry oil density from at least one oil-continuous measurement, and/or
      ii) deriving a corrected estimate of aqueous salinity from at least one water-continuous measurement; and
   d) using said corrected estimates to estimate water-cut.

* * * * *